United States Patent [19]

Lankford

[11] Patent Number: 5,363,839

[45] Date of Patent: Nov. 15, 1994

[54] VIDEO OTOSCOPE

[75] Inventor: James D. Lankford, St. Louis, Mo.

[73] Assignee: JEDMED Instrument Company, St. Louis, Mo.

[21] Appl. No.: 948,097

[22] Filed: Sep. 21, 1992

[51] Int. Cl.$^5$ ............................ A61B 1/22; A61B 1/06
[52] U.S. Cl. ............................................. 128/9; 128/6
[58] Field of Search ................................. 128/4, 6–10

[56] References Cited

U.S. PATENT DOCUMENTS

| | | | |
|---|---|---|---|
| 3,638,643 | 2/1972 | Hotchkiss | 128/9 |
| 3,840,004 | 10/1974 | Heine | 128/9 |
| 4,380,998 | 4/1983 | Kieffer, III et al. | 128/9 |
| 4,712,537 | 12/1987 | Pender | 128/9 |
| 4,740,837 | 4/1988 | Yanagisawa et al. | 358/98 |
| 4,807,594 | 2/1989 | Chatenever | 128/4 |
| 4,851,866 | 7/1989 | Ciarlei et al. | 354/62 |
| 4,867,137 | 9/1989 | Takahashi | 128/6 |
| 4,901,142 | 2/1990 | Ikuno et al. | 358/98 |
| 4,947,245 | 8/1990 | Ogawa et al. | 128/6 X |
| 4,974,580 | 12/1990 | Anapliotis | 128/4 |
| 4,998,182 | 3/1991 | Krauter et al. | 361/394 |
| 5,005,943 | 4/1991 | Fort | 350/96.26 |
| 5,042,915 | 8/1991 | Akutsu et al. | 359/230 |
| 5,125,394 | 6/1992 | Chatenever et al. | 128/4 |

OTHER PUBLICATIONS

Konrad et al., "Pediatric Otoscopy & Photography of the Tympanic Membrane", Arch Otolarynol, 1979, pp. 431–433.

Richard Wolf, Medical Instruments Corp., catalog p. G2, showing Ear Endoscopes.

Welch Allyn, Inc., catalog page showing Otoscopes.

Primary Examiner—Richard J. Apley
Assistant Examiner—John P. Leubecker
Attorney, Agent, or Firm—Haverstock, Garrett & Roberts

[57] ABSTRACT

A video otoscope enables a complete otological examination via high resolution color video to be conducted. The video otoscope includes an otoscope head having a rod lens system and structure enabling mounting a video camera on the otoscope head in position for receiving the rod lens image. The video otoscope also enables mounting a speculum in overlaying relation to the rod lens for retracting the wall of the ear canal, and the use of a pneumatic insufflator bulb in cooperation with both the rod lens and the speculum for demonstrating ear drum mobility. The video otoscope can furthermore include a high resolution color video monitor as well as a video recorder and a multiple or single image printer to enable recording the otological examination.

20 Claims, 3 Drawing Sheets

VIDEO OTOSCOPE

The present invention relates to otoscopes for use in examining the external canal of the ear and the ear drum, and more particularly, to an improved otoscope construction providing rod lens optical means and dedicated high resolution video means in combination with a speculum for retracting or dilating the ear canal and a pneumatic bulb for demonstrating ear drum mobility to enable conducting a complete otological examination by video. The video otoscope provides an otoscope head having an elongated rod lens insertable into the outer ear canal, and can include a light source such as a fiber optic light source for bright yet cool illumination of the ear. The otoscope also provides means for attaching a video camera or other video pick-up device to the otoscope head and can include a color high resolution video monitor. Using the video otoscope, a physician can conduct a complete examination of the ear by viewing a high resolution color image on the video monitor and can diagnose otological pathology without having to first visualize the ear through an eyepiece mounted on the otoscope and then attach a video camera device with an adapter over the eyepiece as required with prior optical otoscopes. The present video otoscope also enables others such as a physician's assistant, the patient and others to view the examination on the video monitor. For documenting the examination, the present video otoscope system can also include a video recorder as well as a printer for producing single or multiple image copies of portions of the examination.

BACKGROUND OF THE INVENTION

Otoscopy is a category of the endoscopy art specifically directed to the examination of the external canal of the ear and the membranes thereof, namely, the tympanic membrane or eardrum. Typical of known otoscope constructions are strictly optical devices which include an optical lens or eye piece through which a user physician views the ear, such as available from Welch Allyn, Inc. of Skananteles Falls, N.Y. Such known optical otoscopes can also include a speculum which is insertable into the ear canal for retracting or dilating the wall of the ear canal and a pneumatic insufflator bulb which can be attached to the otoscope for communicating air under pressure through the speculum and against the ear drum to enable demonstrating the mobility thereof. Still other known optical otoscopes include the capability for attachment of a photographic camera or a video camera over the eyepiece thereof in cooperation with adapter means for converting the visual ready image to a camera ready image to provide photographic or video documentation of the examination, such as available from Richard Wolf Medical Instruments Corp. of Rosemont, Ill., and Karl Storz Endoscopy—America, Inc. of Culver City, Calif. However, an important limitation of the prior art video capabable optical otoscopes is the requirement of adapter means for converting a visually viewable image to a camera viewable image. Furthermore, some known endoscope constructions for uses other than otoscopy include dedicated video capability. However, such prior art endoscopes are limited as they do not include the capability for attachment of a speculum or a pneumatic bulb thereto to enable conducting a complete otological examination. Contrasted to the relatively limited prior art devices discussed above, the present invention provides a dedicated high resolution video otoscope system including both a speculum and a pneumatic insufflator bulb to enable a physician to conduct an entire examination of the ear via real time high resolution video.

SUMMARY OF THE INVENTION

The present invention overcomes many of the limitations and shortcomings of known otoscope and endoscope constructions and teaches the construction and operation of a complete video otoscope system which provides an otoscope head including rod lens optical means including an elongated rod lens portion insertable into a patient's outer ear canal and which rod lens optical means communicate a clear and brightly illuminated image of the ear through the otoscope head to a high resolution color video camera mounted thereon. The rod lens optical means condition the image specially for communication to a video camera and the otoscope head further includes means enabling sharply focusing the image. The otoscope head also includes means for mounting a speculum thereon in overlaying relation to the elongated rod lens portion to enable retracting the wall of the ear canal, and also means for attaching a pneumatic insufflator bulb thereto and means for communicating air under pressure from the pneumatic bulb to the speculum tip to force air against the eardrum to enable observing the responsive movement thereof. The present device provides a high resolution color video camera or other suitable video pick-up device which mounts directly on the otoscope head for receiving the visual image from the optical rod lens means. The present video otoscope system also includes a high resolution color video monitor to enable viewing the examination, and can also include an optional video recorder such as a video cassette recorder, and an optional single image or multiple image format printer, to enable documenting the examination.

An important feature of the present video otoscope system is the capability to attach a speculum to the otoscope head in overlaying relation to the elongated rod lens portion to enable retracting the wall of the ear canal. The speculum can be of conventional construction having a curvilinearly tapering shape extending convergingly toward an opening at the tip of the speculum. The speculum should be of suitable length to receive the elongated rod lens portion such that the terminal or distal end of the rod lens is positioned in or closely adjacent the opening in the tip of the speculum. Importantly, the tip opening should be sufficiently large to provide a space or passageway around the elongated rod lens portion for the passage of air therethrough, as discussed below. A sealed condition should be formed between the mounting means of the otoscope head and the speculum and the speculum should be easily removable from the otoscope head to enable the option of insertion into the ear of the elongated rod lens portion by itself.

Another feature of the present video otoscope is the ability to attach a pneumatic bulb to the otoscope head for providing air under pressure to the otoscope to enable demonstrating ear drum mobility. Importantly, the air under pressure is communicated from the pneumatic bulb to the speculum through a passageway extending through the otoscope head, which passageway extends from an opening adjacent the means for attaching the pneumatic bulb to an opening communicating with the speculum. The otoscope head also includes means for attaching a suitable light source which light source can also form a component of the present video otoscope system. The light source preferably includes a fiber optic cable communicating light from a light source which provides bright yet cool illumination and which light source can be of constant or variable intensity.

The present video otoscope is a dedicated video device which eliminates the prior art requirement of adapter means for converting the optical image for video. This dedicated video capability provides a sharp clear video image which enables a doctor, while viewing the video monitor, to insert the elongated rod lens portion of the otoscope head into the ear canal and safely manipulate and guide the movement of the rod lens portion in the ear. The physician can conduct a thorough examination of the ear by watching the video monitor and can simultaneously make a record of the examination with the optional recording and printing means. The video capability also provides a visual aid for a physician's assistant and others viewing the examination such as the patient or the parent of a pediatric patient, and enables the physician to provide a detailed explanation of the examination and his or her otological diagnosis using the high resolution color video images.

It is therefore a principal object of the present invention to provide means enabling conducting a complete otological examination by viewing a video monitor.

Another object is to enable conducting a video otological examination without having to first visualize the ear through an eyepiece on the otoscope.

Another object is to provide an otoscope having a video capability which does not require use of means for adapting a visual ready image to a camera ready image.

Another object is to provide a dedicated video otoscope which includes means enabling retracting the wall of the outer ear canal.

Another object is to provide a dedicated video otoscope having means enabling demonstrating eardrum mobility.

Another object is to provide an otoscope which enables more than one person to view an otological examination at the same time.

Another object is to provide a video otoscope system providing means for making a video record of an otological examination.

These and other objects and advantages of the present invention will become apparent to those skilled in the art after considering the following detailed specification in conjunction with the accompanying drawings wherein:

DETAILED DESCRIPTION OF THE PREFERRED EMBODIMENT

Figure 1:
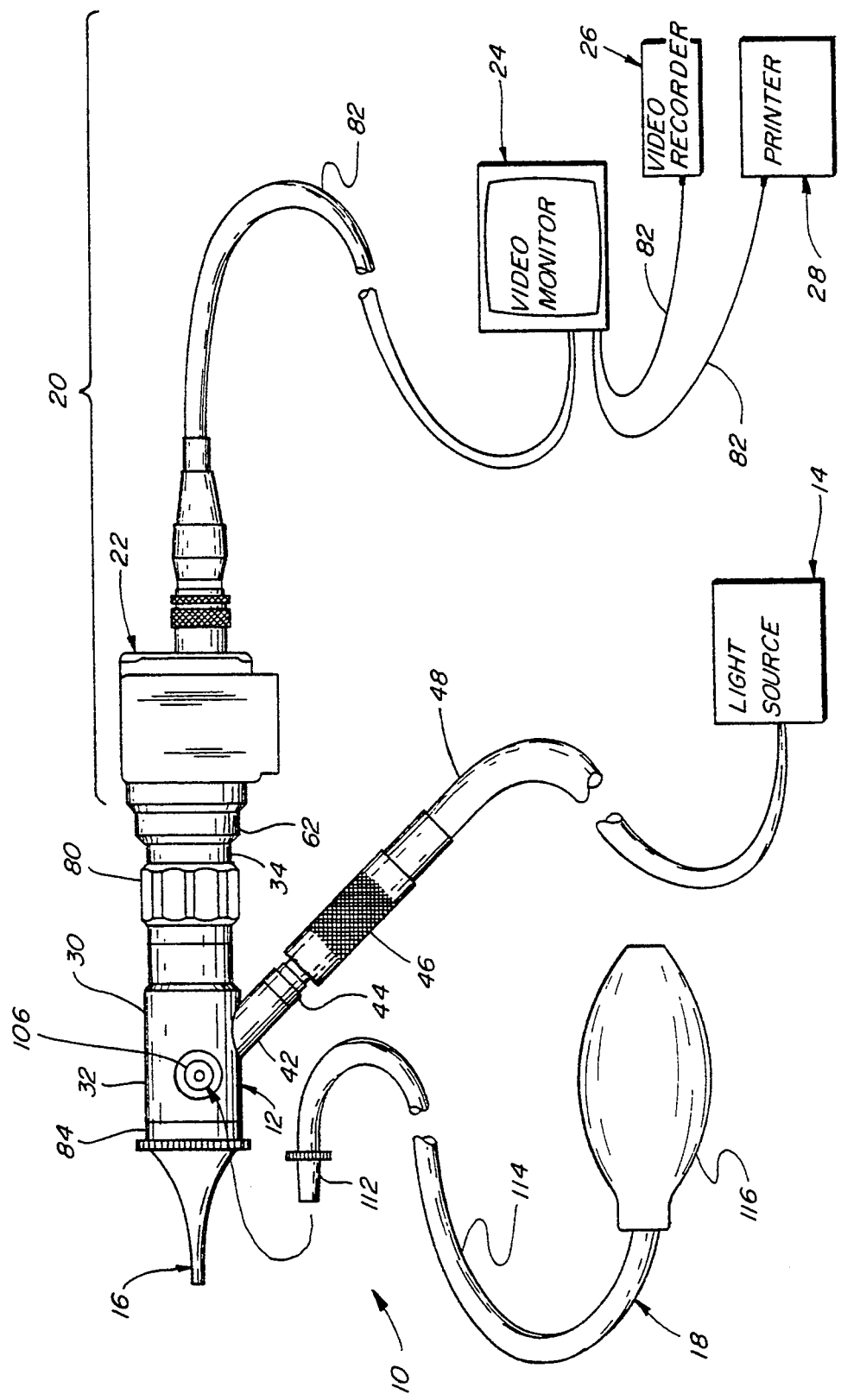
FIG. 1 is a left side elevational view of a video otoscope constructed according to the teachings of the present invention including an otoscope head having a speculum and a video camera mounted thereon and showing in association therewith a light source, a pneumatic insufflator bulb, and video means including a video monitor, an optional video recorder, and an optional single or multiple video image printer.

Referring to the drawings more particularly by reference numbers, wherein like numerals refer to like parts, number 10 in FIG. 1 identifies a video otoscope system constructed according to the teachings of the present invention. The present video otoscope system 10 includes an otoscope head 12; a light source 14; a speculum 16; a pneumatic bulb 18; and high resolution color video means 20 including a video camera 22 communicating with a video monitor 24, an optical video recorder 26, and an optional printer 28. The present video otoscope system 10 includes all of the components necessary for conducting a complete video examination of the outer ear canal and the ear drum.

Figure 2:
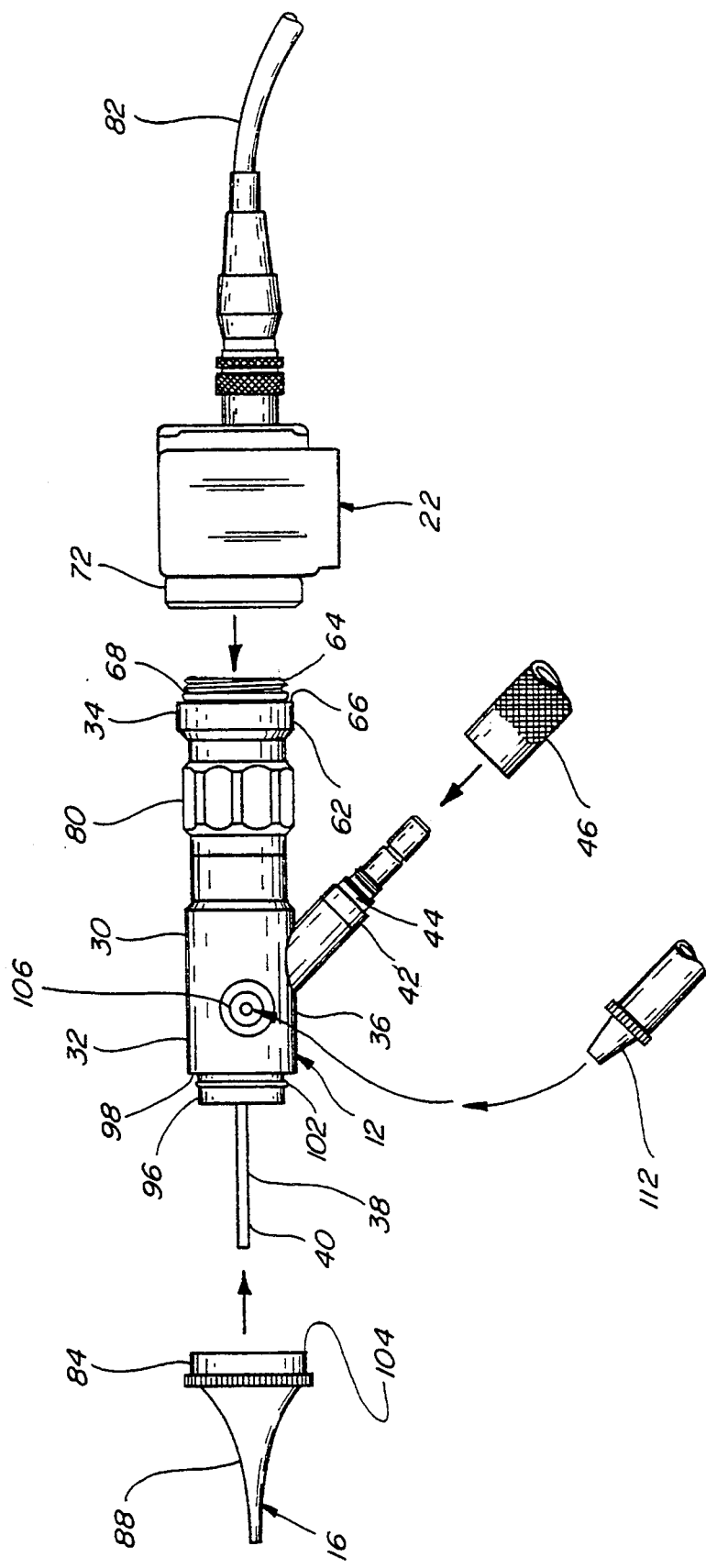
FIG. 2 is a left side elevational view of the otoscope of FIG. 1 in exploded form showing the rod lens portion of the otoscope, the means for attaching the speculum, the means for attaching the video camera, and the means for attaching the light source.

The otoscope head 12 is that portion of the present video otoscope system 10 which is held by a physician or other user and includes rod lens means which are insertable into the ear. Referring to FIG. 2, the otoscope head 12 is formed by a cylindrical shaped base or body member 30 having a first opposite end portion 32, a second opposite end portion 34 and an intermediate body portion 36 extending therebetween. The rod lens means include an elongated rod lens portion 38 which extends outwardly from the otoscope head end portion 32 in concentric relation to the cylindrical otoscope head 12 and terminates at a distal rod end 40. The elongated rod lens portion 38 is a tubular member of rigid construction having a smooth cylindrical or annular shaped outer surface and dimensional characteristics suitable for insertion into the ear. For instance, an elongated rod lens portion 38 having a length of about 34 mm and a diameter of about 2.7 mm has been found to be satisfactory for this purpose.

The otoscope head 12 and the rod lens means communicate light from a light source 14 to the distal rod end 40 for illuminating an ear being examined, and also optical means for communicating a visual or optical image of the ear to the video camera 22. The otoscope head 12 receives light for illuminating the ear through a light post 42 which extends outwardly at an acute angle from the intermediate body portion 36. The light post 42 includes means for attaching a light cable from the light source 14, preferably including a fitting 44 which is cooperatively engageable with a connector 46 on the end of a light cable such as the fiber optic light cable 48 shown in FIG. 1. The light is communicated through the light post 42 into the otoscope head 12 and through the elongated rod lens portion 38 preferably using means such as a fiber optic bundle (not shown). The fiber optic bundle extends through an annular shaped outer bore 50 extending along the length of the elongated rod lens portion 38, which outer bore 50 terminates at an annular shaped opening 52 adjacent the distal rod end 40 (FIG. 3) and from which opening 52 the light is emitted.

Figure 3:
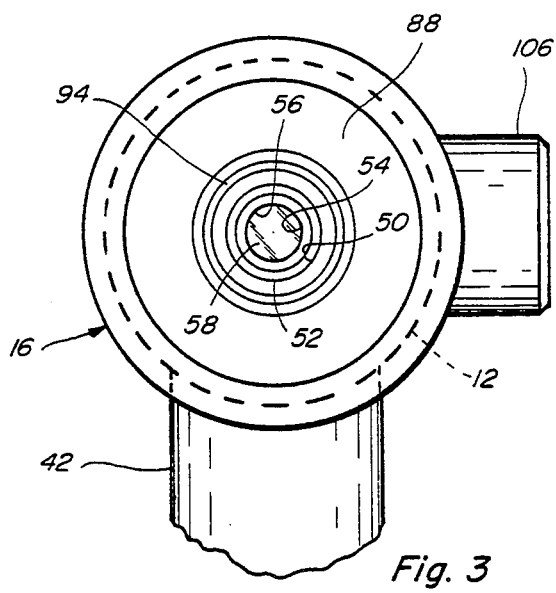
FIG. 3 is an enlarged front elevational view of the otoscope head of FIG. 1 showing and the rod lens through an opening at the speculum tip.
Figure 4:
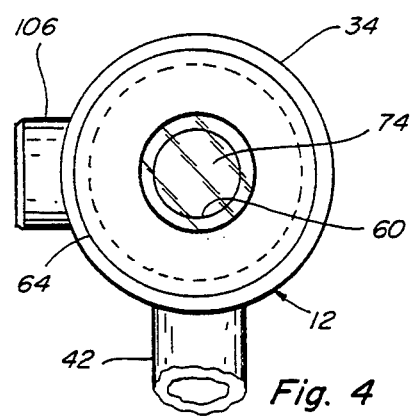
FIG. 4 is an enlarged rear elevational view of the otoscope head showing the camera mounting means and the rear aperture.
Figure 5:
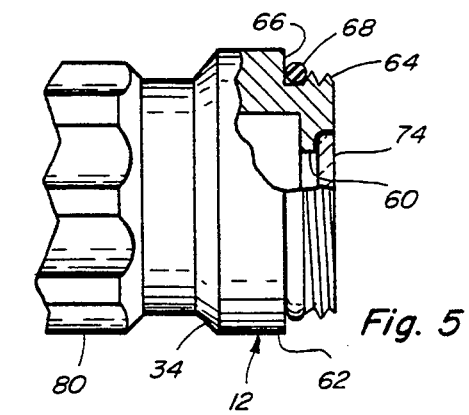
FIG. 5 is an enlarged fragmentary left side elevational view of the otoscope head showing in partial cross-section the camera mounting means.

An image of the ear is communicated in the opposite direction through the elongated rod lens 38 and the otoscope head 12 to the video camera 22 and is conditioned for input to the video camera according to well known optical principles. The image is communicated through the elongated rod lens portion 38 in an inner bore 54 located concentrically and inwardly of the outer bore 50, as shown in FIG. 3. The image enters the inner bore 54 through an opening 56 located adjacent the distal rod end 40, the opening 56 including an optical lens 58. The image passes from the rod lens and through the otoscope head 12 and is emitted from the otoscope head through a rear aperture 60 located adjacent the otoscope head end portion 34, as shown in FIGS. 4 and 5 where the image can be received by the video camera 22.

Figure 6:
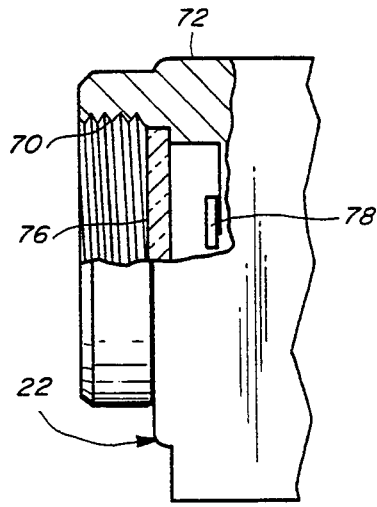
FIG. 6 is an enlarged fragmentary left side elevational view of the video camera in partial cross-section to show the camera end mounting means.

The video camera 22 can be detachably mounted to the otoscope head 12 in position over the rear aperture 60 using camera mounting means 62. The camera mounting means 62 preferably include a universal "C" mount video connector which has a threaded portion 64 and an endwardly facing shoulder 66 adjacent thereto, as best shown in FIG. 5. Importantly, the camera mounting means 62 also include an O-ring 68 located in abutting relation to the shoulder 66, which O-ring 68 is compressible by threaded engagement between the threaded portion 64 on the otoscope head and a threaded portion 70 of camera side mounting means 72 located on the video camera 22, shown in FIG. 6. The compression of the O-ring 68 acts to form a sealed condition between the otoscope head 12 and the video camera 22 and also provides both compressional and frictional forces for maintaining the engagement of the threaded portions 64 and 70 while still enabling relative rotation between the otoscope head 12 and the video camera 22. This importantly enables adjusting the angular orientation of the image received by the video camera 22 which has the desired effect of also changing the angular orientation of the image viewed on the video monitor 24.

With the video camera 22 mounted to the otoscope head 12 in the above described manner and as shown in FIG. 1, the visual or optical image is emitted through an optically clear rear lens 74 located in the rear aperture 60 of the otoscope head (FIG. 5) and is directly received through another optically clear lens 76 on the video camera 22 (FIG. 6) wherein the image impinges an electronic pick-up device 78. The otoscope head 12 further includes means for sharply focusing the visual image on the electronic pick-up 78, which focusing means include an external focusing barrel 80 (FIGS. 1, 2 and 5) rotatable relative to the cylindrical body member 30. The video camera 22 can comprise any commercially available video camera or other video pick-up device suitable for receiving the visual image from the otoscope head 12. For instance, a high resolution color video camera capable of about 470 lines of resolution available from the Elmo Manufacturing Corp. of New Hyde Park, N.Y., has been found to be satisfactory.

The video camera 22 operates in the conventional manner to convert the optical image received thereby into an electronic video signal which is communicated through a video cable 82 to the video monitor 24 wherein the electronic video signal is converted to a high resolution video image. The video monitor 24 can also comprise any suitable commercially available device. For instance, a color television monitor capable of about 420 lines of resolution available from the Panasonic Corp. of Secaucus, N.J. is satisfactory. The video signal can also be communicated via additional cables 82 to an optional video cassette recorder 26, and also to an optional single or multiple video image printer 28. The video cassette recorder can also comprise any suitable commercially available device, and the video image printer 28 can also comprise a commercially available device which can, for instance, digitally store one or more of the video frames and reproduce one or more of the stored frames on thermal paper in color using subliminal dye technology.

Figure 7:
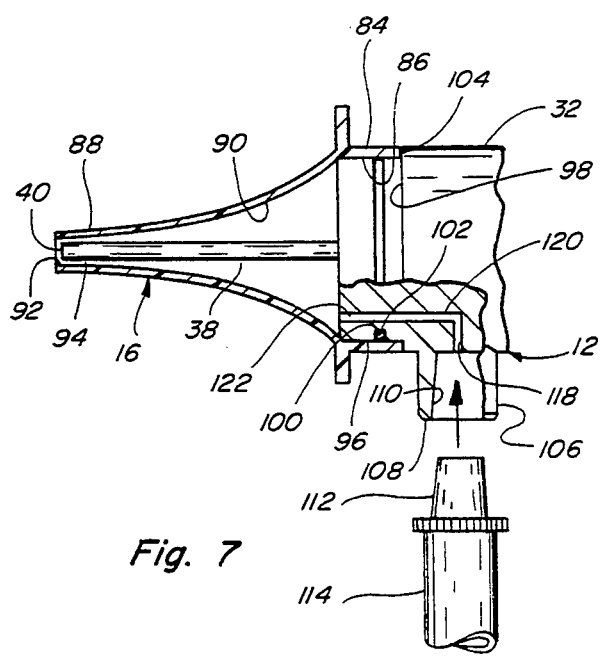
FIG. 7 is an enlarged fragmentary top view of the otoscope head in partial cross-section to show the passageway extending therethrough and showing the speculum in cross-section.

The speculum 16 can be mounted on the otoscope head end portion 32 in overlaying relation to the elongated rod lens portion 38, as shown in FIGS. 1 and 7, to enable retracting or dilating the wall of the ear canal as the speculum 16 and elongated rod lens portion 38 are inserted therein. The speculum 16 is preferably of conventional construction such as available from Welch Allyn of Skaneateles Falls, N.Y. The preferred speculum 16 is an annular shaped member including a base or mounting portion 84 having an annular shaped inner surface 86 defining an opening. Extending outwardly from the base portion 84 is a tip portion 88 having a curvilinearly tapering shape which extends convergingly from the base portion 84. The tip portion 88 has an inner surface 90 which defines an inner cavity communicating the opening of the base portion 84 with a tip end opening 92. Importantly, the length of the speculum 16 should be sufficient such that when the speculum 16 is mounted on the otoscope head 12 in overlaying relation to the elongated rod lens portion 38, the distal rod end 40 is located in or closely adjacent to the tip end opening 92 so as to enable the unobstructed passage of light from the distal rod end 40 to the ear and also an unobstructed view of the ear through the optical lens 58 mounted on the distal rod end. Furthermore, the tip opening 92 should have a diameter sufficiently larger than that of the elongated rod lens portion 38 so as to form an annular shaped space or passage 94 around the distal rod end 40 to enable the passage of air therethrough, as discussed below. A tip end opening 92 having a diameter of about 3 mm has been found to provide a satisfactory annular space 94 for the passage of air around a distal rod end 40 having a diameter of about 2.7 mm, as discussed above.

The means for mounting the speculum 16 on the otoscope head end portion 32 include a cylindrical or annular shaped outer surface 96 located in concentric relation with the elongated rod lens 38. The cylindrical or angular shaped outer surface 96 extends axially from adjacent the otoscope head end portion 32 toward the opposite end portion 34 and terminates at a shoulder 98. The outer annular surface 96 can taper radially outwardly toward the shoulder 98 and is sized and shaped for receiving the base portion 84 of the speculum 16. The outer annular surface 96 includes an O-ring groove 100 formed therein, in which groove 100 is located an O-ring 102 which engages the inner annular surface 86 of the speculum 16. The O-ring 102 is compressible by engagement with the speculum for frictionally maintaining the speculum 16 on the otoscope head 12 and also to form an airtight or nearly airtight seal around the inner periphery of the base portion 84. The shoulder 98 is located a predetermined distance from the distal rod end 40, which distance corresponds approximately to the length of the speculum 16 such that when the endmost edge 104 of the speculum 16 is located in abutting relation with the shoulder 98, the distal rod end 40 will be located closely adjacent to or in the tip end opening 92.

Still referring to FIG. 7, the otoscope head 12 also includes means 106 for attaching a pneumatic bulb 18. The means 106 preferably include a sidewardly extending fitting 108 at an intermediate location on the otoscope head, the fitting 108 having a tapered annular inner surface 110 which defines a receptacle for cooperatively receiving and engaging a nipple 112 on the pneumatic insufflator bulb 18. The pneumatic insufflator bulb 18 can comprise any suitable commercially available insufflator bulb, for instance, as available from Welch Allyn, and typically includes a tube 114 communicating the nipple 112 with a compressible or squeezable bulb 116, as shown in FIG. 1.

The otoscope head 12 includes means for communicating air under pressure from a pneumatic insufflator bulb 18 mounted on the fitting 108 to the inner cavity 90 of the speculum 16. The means for communicating air through the otoscope head 12 include an opening 118 communicating with the receptacle on the fitting 108, which opening 118 communicates with a passageway 120 extending through a portion of the otoscope head 12. The passageway 120 extends from the opening 118 to a second opening 122 located on the otoscope head end portion 32, which second opening 122 is located in communication with the inner cavity 90 of the speculum 16.

To use the present video otoscope system 10, with the video means mounted on the otoscope head 12 and the light source 14 in communication therewith, the user physician can insert the elongated rod lens portion 38 into the patient's outer ear canal while guiding the movement and manipulation thereof via the image displayed on the video monitor 24. The ear is brightly illuminated by the light emitted from the distal end of the elongated rod lens and the image of the ear can be sharply focused by rotating the focusing barrel 80 to enable clear viewing for accurate diagnosis of otological conditions. Furthermore, to enable retracting the wall of the ear canal during the examination, the speculum 16 can be quickly and easily mounted in overlaying relation to the elongated rod lens prior to insertion. Still further, to enable demonstrating eardrum mobility, the pneumatic bulb 18 can be attached to the otoscope head. The compressible bulb 116 can then be squeezed to force air under pressure through the passageway 120 in the otoscope head 12 and into the cavity 90 of the speculum 16, where the pressurized air can exit through the annular opening 94 around the distal rod end 40 and impinge the ear drum as the physician views any responsive movement of the eardrum on the monitor.

With an optional video cassette recorder 26 receiving the electronic video signal from the video camera 22, a user can produce a video record of all or part of the otological examination to enable viewing it at a later time. Furthermore, with an optional single or multiple image printer 28, one or more of the video image frames can be stored in the printer 28 and reproduced on paper.

Thus there has been shown and described a video otoscope system which fulfills all of the objects and advantages sought therefor. Many changes, modifications, variations, and other uses and applications of the present construction will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A video otoscope head comprising a body member having first and second opposite end portions, an elongated rod lens extending outwardly from the first end portion of said body member and terminating at a distal rod end, the second end portion of said body member having a rear aperture through which an image from said rod lens can be transmitted, means for mounting a video camera on the second end portion of said body member in position to enable directly receiving an image from said rod lens through said rear aperture, means for attaching a light source to said body member at an intermediate location between said first and second opposite end portions, means in said body member and adjacent said rod lens for communicating light from said means for attaching a light source to the distal rod end of said rod lens, a fitting for attaching a pneumatic bulb to said body member at an intermediate location between said first and second opposite end portions, said body member having a passageway extending between a first opening communicating said passageway with said fitting and a second opening communicating with the first end portion of said body member, said fitting enabling air under pressure exhausted from a pneumatic bulb attached thereto to pass into the first opening and into said passageway, and said body member including means for mounting a speculum adjacent the first end portion of said body member and a speculum, having a tip end opening of known size, mounted to said mounting means in overlaying relationship to both said elongated rod lens and said second opening, said speculum mounting means including surface means engageable with a surface on the speculum located a known distance from the tip end opening thereof, said surface means being located a distance from the distal rod end of said rod lens corresponding to said known distance such that the distal rod end will be located substantially coterminous with the tip end opening of the speculum when the speculum is mounted over the rod lens, said distal rod end having a size which is sufficiently smaller than the known size of the speculum tip end opening such that the tip end opening will form a space around the distal rod end when the speculum is mounted over the rod lens, air under pressure from a pneumatic bulb introduced into said passageway through the first opening being capable of passing through the passageway, through the second opening and through a speculum mounted on the body member and exiting the speculum through the space around the distal rod end.

2. The video otoscope head of claim 1 further including seal means for forming a sealed condition between the first end portion of said body member and said speculum mounted adjacent thereto.

3. The video otoscope head of claim 2 wherein said seal means include an O-ring.

4. The video otoscope head of claim 1 further including a video camera mounted adjacent the second end portion of said body member.

5. The video otoscope head of claim 4 further including a video monitor connected in communication with said video camera.

6. The video otoscope head of claim 1 further including a light source, said light source including a fiber optic cable attachable to said means for attaching a light source to said body member.

7. The video otoscope head of claim 1 further including pneumatic bulb means attached to said fitting.

8. The video otoscope head of claim 1 wherein said speculum has a base portion and a tip portion, said base portion being mountable on said speculum mounting means on said body member and including said surface engageable with said surface means of said mounting means, said tip opening being located on said tip portion opposite said base portion.

9. A video otoscope comprising an otoscope head having first and second opposite end portions, rod lens means including an elongated rod lens portion extending outwardly from the first end portion of said otoscope head and terminating at a distal rod end, means for mounting a speculum adjacent said first end portion of said otoscope head in said speculum mounting means including surface means located a predetermined distance from said distal rod end, video camera means mounted on the second end portion of said otoscope head in position for receiving an image directly from said rod lens means, means on said otoscope head for attaching a light source to said otoscope head, and means in said otoscope head and in said rod lens portion for communicating light from said means for attaching a light source to said distal rod end, a speculum mounted on said otoscope head in overlaying relation to said elongated rod lens portion, said speculum having a base portion for mounting on the otoscope head and a tip portion defining an inner cavity for receiving the elongated rod lens portion, said base portion having an end surface engageable with said surface means of said speculum mounting means, said tip portion including a terminal end portion located opposite said base portion, said terminal end portion having a tip opening of predetermined size communicating with said inner cavity, said tip opening being located a predetermined distance from the end surface of said base portion corresponding to the predetermined distance from said surface means to said distal rod end such that said distal rod end is positioned in said tip opening when the speculum is mounted on the otoscope head, said distal rod end being correspondingly smaller than said tip opening such that said tip opening forms a space around said distal rod end, and means for attaching a pneumatic insufflator bulb to said otoscope head intermediate the first and second opposite end portions thereof, said otoscope head having a passageway extending through a portion thereof, said passageway communicating the inner cavity of said speculum with said pneumatic insufflator bulb attachment means, said pneumatic insufflator bulb attachment means enabling air under pressure from an insufflator bulb to enter said passageway wherein said air under pressure is directed into said speculum and exhausted through said tip opening around said distal rod end.

10. The video otoscope of claim 9 further including seal means on said otoscope head for forming a sealed condition between said otoscope head and said speculum mounted thereon.

11. The video otoscope of claim 9 further including a pneumatic insufflator bulb attachable to said pneumatic insufflator bulb attachment means located on said otoscope head, said pneumatic insufflator bulb being capable of communicating air under pressure through the otoscope head passageway and into the inner cavity of said speculum for passage through the space around the distal rod end and through the tip opening of said speculum.

12. A video otoscope comprising:

an elongated otoscope head having first and second opposite end portions and an intermediate portion extending therebetween, rod lens means on said otoscope head including an elongated rod lens portion extending outwardly from the first opposite end portion thereof, said elongated rod lens portion terminating at a distal rod end, means on said otoscope head for receiving light from a light source and communicating the light through said otoscope head and through said elongated rod lens means and thereafter emitting the light at the distal rod end, means adjacent the first end portion of said otoscope head for mounting a speculum in overlaying relationship to said elongated rod lens portion including an annular shoulder portion positioned and located at a predetermined distance from the distal rod end, means for attaching a pneumatic bulb to said otoscope head, and means for mounting a video camera on the second end portion of said otoscope head in position for receiving a visual image from said rod lens means, a speculum including a base portion having means thereon for cooperatively engaging the speculum mounting means on said otoscope head, said speculum base portion having an annular edge located to abut the shoulder portion of said otoscope head when said speculum is engaged therewith, said speculum further including a tip portion extending outwardly from said base portion, said tip portion having a tapered shape defining an inner cavity for receiving said elongated rod lens means and a terminal end portion located opposite said base portion, said tip portion including a tip opening communicating with said inner cavity, said speculum having a length measured from the edge of said base portion to the tip opening, the predetermined distance from the shoulder on the otoscope head to the distal end portion of said elongated rod lens portion corresponding to the length of the speculum such that when the speculum is mounted on said otoscope head, the distal rod end of said elongated rod lens means is located substantially in said tip opening, said distal rod end being sufficiently smaller than said tip opening so as to form a space around said distal rod end, a passageway formed in said otoscope head, said passageway extending between the pneumatic bulb attachment means and the first end portion of said otoscope head, said passageway communicating the inner cavity of the speculum tip portion with the pneumatic bulb attachment means, said pneumatic bulb attachment means enabling the passage of air to said passageway, pneumatic bulb means attached to said otoscope head, said pneumatic bulb means being squeezable to communicate air under pressure into the passageway of said otoscope head and into the inner cavity of said speculum for passage through the space around the distal rod end and through the tip opening of said speculum, and a video camera attached to said video camera mounting means on said otoscope head.

13. The video otoscope of claim 12 further including a video monitor including means for communicating the video monitor with the video camera.

14. The video otoscope of claim 13 wherein the video camera mounting means on said otoscope head include a threaded member threadedly engageable with a threaded member on the video camera enabling a video camera threadedly attached to said mounting means to be rotated relative to the otoscope head for adjusting the orientation of a video image on the video monitor.

15. The video otoscope of claim 12 wherein said means for mounting a video camera adjacent the second end portion of said otoscope head includes a universal "C" mount.

16. The video otoscope of claim 12 wherein said speculum mounting means on the otoscope head includes a groove formed therein, and an O-ring positioned and located in said groove for forming a sealed condition between the otoscope head and the speculum when said speculum is mounted on said otoscope head.

17. The video otoscope of claim 12 further including means on the otoscope head for enabling the focusing of a visual image on the video camera.

18. The video otoscope of claim 12 further including a light source and a fiber optic cable for communicating light from the light source to said light receiving means on the otoscope head.

19. The video otoscope of claim 12 further including a video recorder including means for communicating the video recorder with the video camera.

20. The video otoscope of claim 12 further including a printer capable of reproducing at least one video frame including means for communicating the printer with the video camera.

* * * * *